United States Patent
Chesnin et al.

(10) Patent No.: US 8,348,899 B2
(45) Date of Patent: Jan. 8, 2013

(54) METHODS FOR INSERTING A CATHETER

(75) Inventors: Kenneth J. Chesnin, Philadelphia, PA (US); Michael J. Cellini, Wayne, PA (US); Timothy M. Schweikert, Levittown, PA (US)

(73) Assignee: Medical Components, Inc., Harleysville, PA (US)

(*) Notice: Subject to any disclaimer, the term of this patent is extended or adjusted under 35 U.S.C. 154(b) by 49 days.

(21) Appl. No.: 12/905,749

(22) Filed: Oct. 15, 2010

(65) Prior Publication Data
US 2011/0034875 A1 Feb. 10, 2011

Related U.S. Application Data

(62) Division of application No. 11/372,571, filed on Mar. 10, 2006, now Pat. No. 7,871,398.

(60) Provisional application No. 60/660,377, filed on Mar. 10, 2005.

(51) Int. Cl.
*A61M 5/178* (2006.01)
(52) U.S. Cl. .......................... 604/158; 604/161
(58) Field of Classification Search .............. 604/158, 604/160–161, 164.01–164.02, 164.05, 164.07, 604/164.13, 171, 500, 506, 168.01
See application file for complete search history.

(56) References Cited

U.S. PATENT DOCUMENTS

| | | | |
|---|---|---|---|
| 3,633,579 A * | 1/1972 | Alley et al. ............... | 604/508 |
| 4,601,697 A | 7/1986 | Mammolenti et al. | |
| 4,692,141 A | 9/1987 | Mahurkar | |
| 4,738,658 A | 4/1988 | Magro et al. | |
| 4,775,371 A | 10/1988 | Mueller, Jr. | |

(Continued)

FOREIGN PATENT DOCUMENTS
WO 99/42156 A1 8/1999

OTHER PUBLICATIONS

Supplementary European Search Report dated Feb. 16, 2011; European Application No. 06737624.4 (7 pages).

(Continued)

*Primary Examiner* — Theodore Stigell
(74) *Attorney, Agent, or Firm* — Glenn M. Massina, Esq.; Fox Rothschild LLP

(57) ABSTRACT

Catheter assembly (100) having at least one lumen (150 or 160) and joined to hub (106). While the lumen inner diameter(s) remain constant from distal end (144) of the catheter (140) to proximal end (142), the outer catheter diameter increases proximate the hub (106) providing increased resistance to kinking during connection and disconnection from medical apparatus. The increased proximal catheter diameter preferably is sufficiently large to plug the proximal end of an introducer sheath through which the catheter is inserted during patient placement, to plug the proximal sheath end and minimize blood aspiration therethrough, and later serves to fill the vascular insertion upon complete catheter insertion after removal of the introducer sheath again to minimize blood aspiration through the vascular incision. The catheter may have two lumens (150,160) or more, joined to respective extension tubes in hub (106). The two lumens may each have a respective inner diameter of between about 0.020 in and 0.025 in. The catheter body may have a lengthy distal portion vascularly implanted having an appropriate outer diameter for the vessel, and also a lengthy proximal portion with a larger diameter for resistance to kinking at a sharp bend between the vascularly implanted portion and the subcutaneously tunneled lengthy proximal portion.

3 Claims, 3 Drawing Sheets

U.S. PATENT DOCUMENTS

| | | | |
|---|---|---|---|
| 5,020,543 | A | 6/1991 | Rothenberg et al. |
| 5,167,623 | A | 12/1992 | Cianci et al. |
| 5,219,335 | A | 6/1993 | Willard et al. |
| 5,221,263 | A * | 6/1993 | Sinko et al. .................. 604/161 |
| 5,364,344 | A | 11/1994 | Beattie et al. |
| 5,478,326 | A | 12/1995 | Shiu |
| 5,531,719 | A | 7/1996 | Takahashi |
| 5,676,659 | A | 10/1997 | McGurk |
| 5,800,409 | A | 9/1998 | Bruce |
| 5,830,196 | A | 11/1998 | Hicks |
| 5,851,203 | A | 12/1998 | van Muiden |
| 5,895,378 | A | 4/1999 | Nita |
| 6,030,369 | A | 2/2000 | Engelson et al. |
| 6,045,547 | A | 4/2000 | Ren et al. |
| 6,280,423 | B1 | 8/2001 | Davey et al. |
| 6,595,966 | B2 | 7/2003 | Davey et al. |
| 6,719,749 | B1 | 4/2004 | Schweikert et al. |
| 6,796,991 | B2 | 9/2004 | Nardeo |
| 6,827,710 | B1 | 12/2004 | Mooney et al. |
| 2003/0204179 | A1 | 10/2003 | Davey et al. |

OTHER PUBLICATIONS

Office Action dated May 31, 2011; Japanese Patent Application No. 2008-500930 and translation (5 pages).

Information Disclosure Statement from U.S. Appl. No. 11/372,571 dated Sep. 13, 2007 (17 pages).

International Search Report, PCT/US06/08464, mailed Jul. 21, 2006 (4 pages).

Written Opinion, PCT/US06/08464, mailed Jul. 21, 2006 (3 pages).

Preliminary International Search Report, dated Sep. 20, 2007, PCT/US06/008464 (5 pages).

Extended Search Report and Opinion dated Feb. 16, 2011; EP Application No. 06737624.4 (7 pages).

Communication dated Dec. 12, 2011; European Patent Appln. No. 06737624.4.

* cited by examiner

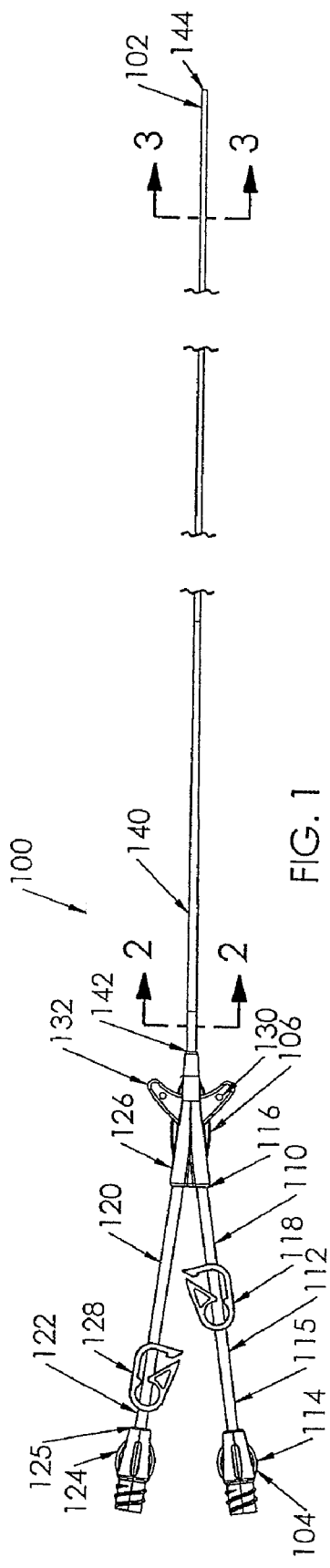
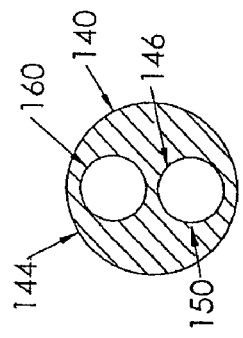
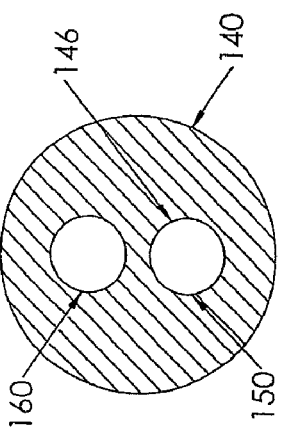
FIG. 1
FIG. 2
FIG. 3

METHODS FOR INSERTING A CATHETER

CROSS-REFERENCE TO RELATED APPLICATION

This application is a Divisional application of U.S. patent application Ser. No. 11/372,571 filed Mar. 10, 2006, now U.S. Pat. No. 7,871,398, issued Jan. 18, 2011 which claims the benefit of U.S. Provisional Application No. 60/660,377 filed Mar. 10, 2005.

FIELD OF THE INVENTION

The invention relates to medical devices and more particularly to catheters and catheter assemblies.

BACKGROUND OF THE INVENTION

Catheter assemblies, and particularly catheter assemblies for use in hemodialysis, are known that have one, two or more lumens extending from a distal end to a proximal end, where the distal end is placed in a blood vessel of a patient, such as the jugular vein, with the proximal end extending from the patient for each lumen to be connected to a respective conduit of a hemodialysis machine. Customarily, each lumen of the catheter assembly is first connected to a respective extension tube within a hub body, and the extension tube is terminated in a luer connector to facilitate connection with and disconnection from the conduit of the hemodialysis machine and commonly the extension tube has disposed therealong a clamp, such as a Roberts clamp, for temporarily closing the conduit when necessary. Implanted catheter assemblies are connected to medical apparatus such as hemodialysis apparatus through the luer connectors, and then disconnected therefrom, all through many cycles; such connection and disconnection involves the catheter assembly undergoing many cycles of stress and strain especially focused at the proximal end where the catheter proximal end enters the hub which connects the catheter lumens to respective extension tubes, or where a single lumen catheter enters its luer connector directly instead of via a hub and extension tube.

It is desired to provide an assurance against occluding or kinking of the catheter lumens, as well as greater strength, at the connection of the catheter and the hub, or at the connection of a single lumen catheter luer connection where no hub is utilized.

Certain catheter assemblies, termed PICC catheters (for peripherally inserted central catheters), are implanted through a vessel entry on an arm of the patient, known as axillary placement. But, usually, the catheter assembly is secured to the torso of the patient in a manner to prevent any dislocation of the distal tips of the catheter lumens from any movement along the vessel after initial placement at the catheterization site. This manner of securement is usually accomplished by a process termed tunneling, in which the proximal portion of the catheter assembly outside of the vessel is tunneled subcutaneously near the vessel entry site, typically beneath the clavicle of the patient, whereafter the hub is sutured or otherwise secured to the patient. By this process, during the connection with and disconnection from the hemodialysis machine of the extension tubes, there is no stress or strain passed to the distal end of the catheter assembly that might tend to dislodge the distal lumen tips from the desired location along the vessel.

The orientation of the tunneled portion of the catheter assembly is not axially aligned with the distal portion of the catheter assembly and in fact a relatively sharp bend may be made in the catheter assembly distally of the tunneled portion during placement.

It is desired to provide an assurance against occluding or kinking in the sharp bend between the tunnel's distal end and the venotomy.

When a catheter is being inserted vascularly into a patient, and the incision is made into the vessel at the access site or venotomy, and the introducer sheath is placed to maintain open the vascular access site for introduction of the catheter assembly, the catheter assembly is initially inserted along the guide wire through the introducer sheath. During this process, aspiration of blood occurs and measures must be taken to temporarily stop the flow, such as manually closing off the proximal end of the introducer sheath. But as the catheter is inserted into the sheath, additional blood again begins to extrude from the sheath.

It is desired to provide a means for minimizing the flow of blood as the catheter assembly is inserted through the introducer sheath and into the vessel, and also after catheter insertion as the introducer sheath is removed from the access site.

Catheters are conventionally produced in various sizes depending on desired uses, and their outer diameters are measured in units termed "french" or "F", with one F equaling 0.013 inches or 0.32 millimeters. The largest sized catheters utilized for vascular placement may have an outer diameter of about 17 F, while the smallest sized dual-lumen catheters presently preferred are 5 F although smaller sized single lumen catheters are known. Certain problems are associated with catheters after they are vascularly in a patient; for example, development of phlebitis and thrombosis is known when the catheter outer diameter is almost the same size as the inner diameter of the vessel within which it is implanted.

It is desired to provide a catheter with a very small outer diameter, especially a dual lumen catheter, thereby minimizing the tendency of phlebitis or thrombosis or the like, to develop.

BRIEF SUMMARY OF THE INVENTION

The present invention provides a catheter assembly wherein the catheter outer diameter is enlarged for at least some of its length proximate the proximal end adjacent the hub, relative to the remainder of the catheter extending to the distal end. The inner diameter of the lumen or lumens remains constant; in a dual-lumen catheter, the inner septum wall between the lumens may also increase in thickness. The increasing diameter of the catheter in the enlarged proximal portion enables the catheter to plug the proximal end of the introducer sheath during later stages of catheter insertion, minimizing blood flow. The increased diameter in the tapered proximal portion also enables the catheter to plug the vascular incision after the introducer sheath has been removed, again minimizing blood flow as the catheter has been fully inserted vascularly.

Another embodiment of the present invention provides a longer larger diameter proximal catheter section for implantation and subcutaneous tunneling in the chest of a patient, in which the larger diameter proximal portion extends to the venotomy, whereby the larger catheter diameter is robust through the sharp curve assumed between the tunnel distal end and the venotomy.

In another aspect of the present invention, a very small diameter dual lumen catheter provides two very small diameter lumens each sufficiently large for an 0.018 inch guide wire, and which may have a catheter outer diameter of more than 3 F and less than 5 F, less likely to induce phlebitis, thrombosis or the like after implantation. This very small diameter catheter also would benefit from the enlarged proximal end diameter, for resistance to occlusion and kinking.

The present invention also comprises a method of inserting a catheter, wherein a catheter having at its proximal end a tapered section extending distally from the proximal end a limited distance with the catheter having a first outer diameter for most of its length, and its proximal end having a second, greater diameter; inserting the catheter through an introducer sheath and into vasculature of the patient until the tapered proximal end portion of the catheter enters the proximal end opening of the introducer sheath and closes off the opening, whereafter the introducer sheath may now be split and removed as the catheter continues to be inserted into the vasculature until the tapered proximal end portion reaches and substantially closes off the vascular incision.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a top plan view of a multi-lumen catheter assembly according to the present invention;

FIG. 2 is an enlarged sectional view of the lumens of the multi-lumen catheter assembly taken along lines 2-2 of FIG. 1;

FIG. 3 is an enlarged sectional view of the lumens of the multi-lumen catheter assembly taken along lines 3-3 of FIG. 1;

DETAILED DESCRIPTION OF THE INVENTION

Figure 4:
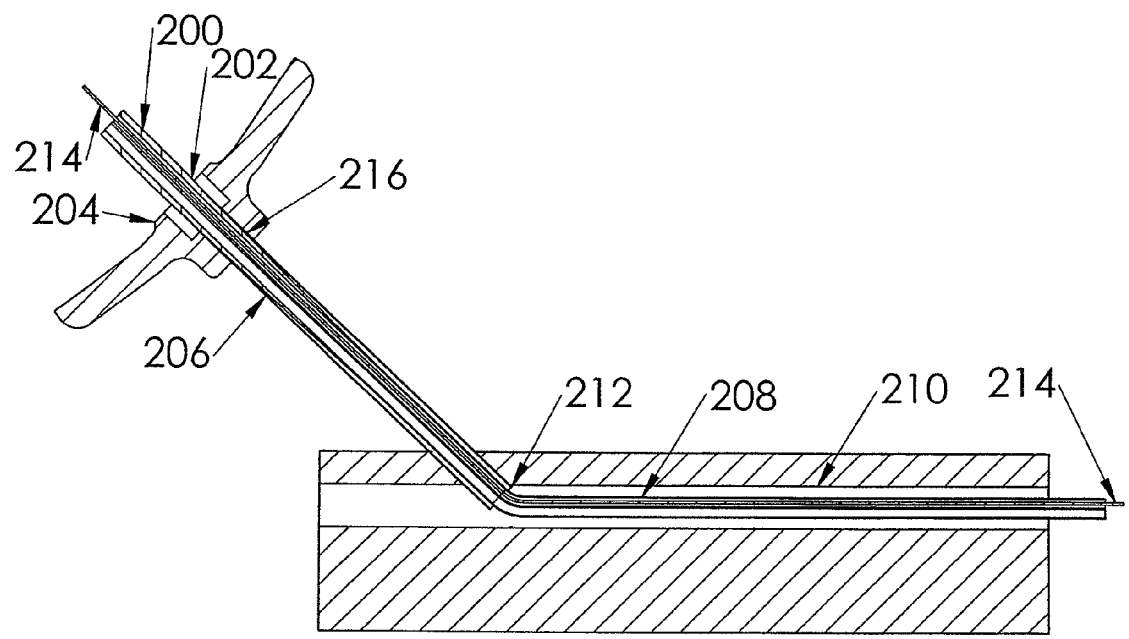
FIG. 4 is a cross-sectional view of the catheter inserted into the introducer sheath during patient placement.

In the drawings, like numerals indicate like elements throughout. Certain terminology is used herein for convenience only and is not to be taken as a limitation on the present invention. The terms "distal" and "proximal" refer, respectively, to directions closer to and farther away from, respectively, an insertion end of the catheter of the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Referring now to FIG. 1, a catheter assembly 100 according to the present invention is shown, having a distal end 102 and a proximal end 104. While catheter assembly 100 is shown and described as having two lumens, the present invention also is beneficial to single lumen catheters or catheters with more than two lumens. A hub 106 connects the distal end 102 and the proximal end 104, and the proximal end 104 includes first and second extension tube assemblies 110, 120, respectively. The first extension tube assembly 110 includes an extension tube 112 having a luer connection 114 fixedly connected to a proximal end 115 of the extension tube 112. A distal end 116 of the extension tube 112 is fixedly connected to the hub 106. A clamp 118, such as a Roberts clamp, is disposed over the extension tube 112 between the proximal end 115 and the distal end 116.

The second extension tube assembly 120 includes an extension tube 122 having a luer connection 124 fixedly connected to a proximal end 125 of the extension tube 122. A distal end 126 of the extension tube 122 is fixedly connected to the hub 106. The clamp 128 is disposed over the extension tube 122 between the proximal end 125 and the distal end 126. The hub 106 fluidly connects the extension tube assemblies 110, 120 with the distal end 102 of the catheter assembly 100. The hub 106 includes suture wings 130, 132 that are used to suture the hub 106 to a patient's skin after insertion.

The distal end 102 includes a dual lumen catheter 140 that includes a catheter proximal end 142 that is fixedly connected to the hub 106 and a catheter distal end 144 that is inserted into vasculature of a patient. As can be seen from FIGS. 2 and 3, the catheter 140 has a generally circular cross section. The catheter 140 tapers from a larger diameter to a smaller diameter in a proximal to distal direction, meaning that the catheter 140 is thicker proximate to the hub 106 at the catheter proximal end 142 than at the catheter distal end 144. Preferably, the catheter has a tapered proximal portion that extends from the larger diameter adjacent the hub for about from 5 cm to 15 cm, and preferably about 10 cm, whereafter the catheter diameter is constant extending to the distal end portion, which also may be tapered to an even smaller distal tip diameter, or have spaced distal tips for the respective lumens. Typical diameters for one particular useful embodiment of the catheter of the present invention, for use with peripherally inserted central catheters, or PICCs, are that the general diameter of the catheter is less than 5 F, such as about 4 F, and the larger diameter adjacent the hub is about 7 F; and where the general diameter is 3 F, the larger diameter is about 4 F; wherein with such small diameters the catheter would be less prone to inducing phlebitis or thrombosis or the like.

Referring to FIGS. 1 to 3, the catheter 140 includes a first lumen 150 that fluidly communicates with the first extension tube 110 through the hub 106 and a second lumen 160 that fluidly communicates with the second extension tube 120 through the hub 106. The first lumen 150 and the second lumen 160 are each generally rounded within the catheter 140. While the catheter 140 tapers along its length, the diameters of each of the lumens 150, 160 remain, within manufacturing tolerances, constant.

The generally rounded lumens 150, 160 enhance fluid flow through the catheter 140 and eliminate corners which encourage blood clotting within the lumens. Preferably, the lumens 150, 160 are sized to allow a 0.018" guide wire to pass with minimal resistance through either lumen 150, 160, such as having diameters of between 0.020 in and about 0.025 in or 0.030 in. A septum 146 separates the first and second lumens 150, 160. Nearer to the proximal end 142 of the catheter 140, the septum 146 is shown as being thicker than nearer to the distal end 144 of the catheter 140. The septum 146 is preferably centered throughout the catheter 140.

The larger diameter of the catheter 140 at the proximal end 142, along with the constant diameter of the lumens 150, 160 housed within the catheter 140, reduces the likelihood of kinking of the lumens 150, 160 nearer to the proximal end 142, especially during handling when the proximal end luer connectors are connected to or disconnected from medical apparatus such as hemodialysis apparatus or the like, while just distally of the hub 106 the catheter 140 enters the subcutaneous tunnel (see FIGS. 4 to 6) and thus is held fixed in position.

In FIG. 4, a catheter assembly 200 is shown, wherein its tapered proximal end portion 202 is entering the proximal end 204 of an introducer sheath 206 during vascular insertion of the catheter distal portion 208, which is mostly already in the vessel 210 with the use of a guide wire 214, entering at venotomy or vascular incision 212. It is seen that the proximal end portion 202 has been inserted until at some location along the tapered portion the proximal end portion 202 has filled the proximal opening 216 of the introducer sheath 206, thus closing off the opening 216 to stop any aspiration of blood therethrough. At this point, the introducer sheath may begin to be split manually along longitudinally extending opposed frangible sections or weaknesses such as grooves (not shown) as the catheter is continuously urged distally to continue to close off the remaining unsplit portion of the sheath, and so on until the sheath is fully split apart and discarded.

Figure 5:
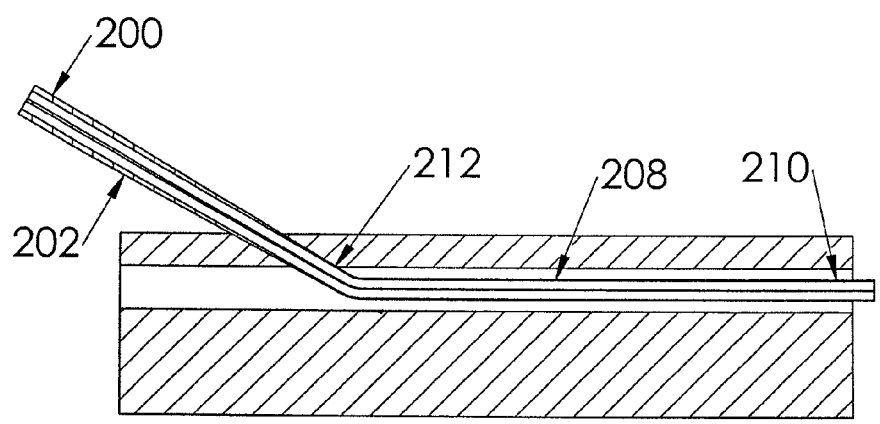
FIG. 5 is a cross-sectional view of the catheter proximal end fully inserted adjacent the vascular incision after sheath removal.

Similarly, in FIG. 5, catheter assembly 200 is shown after introducer sheath 206 of FIG. 4 has been split and removed from about the catheter, and the catheter assembly has been implanted fully into the vessel 210 and the guide wire 214 removed. The proximal end portion 202 has now become moved to be adjacent and partially into the vascular incision 212, and is seen to substantially plug and close off the vascular incision.

Figure 6:
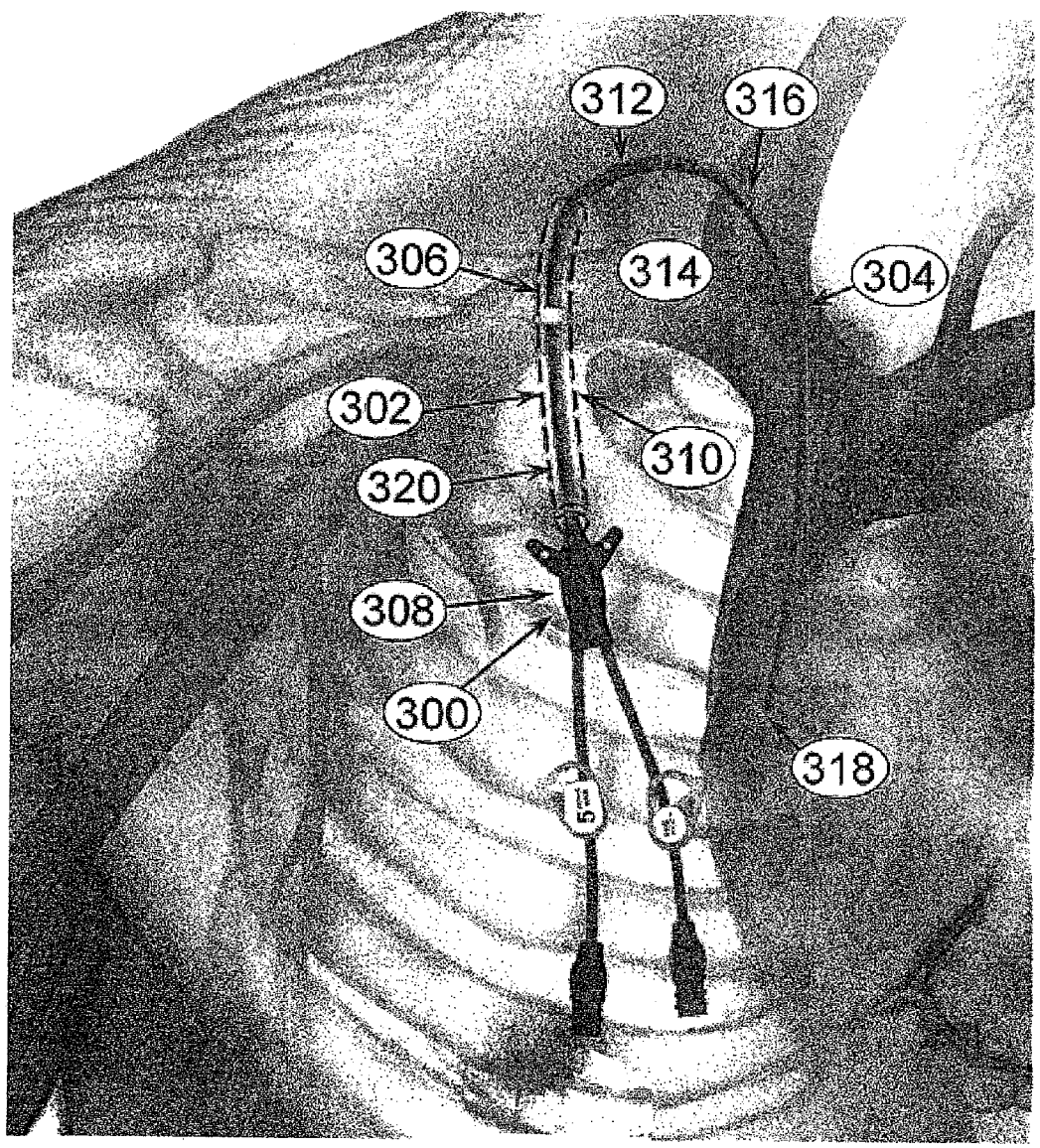
FIG. 6 is an isometric view of an alternate embodiment of the present invention with a longer larger diameter proximal catheter section implanted and subcutaneously tunneled in a patient.

FIG. 6 illustrates an alternate embodiment of the present invention. Catheter assembly 300 is shown implanted and subcutaneously tunneled in a patient. Catheter 302 has a lengthy distal portion 304 with an outer diameter appropriate for the vessel of the patient, and a lengthy proximal, tunneled portion 306 with a generally constant greater diameter from the hub 308 through the tunnel 310 and about the sharp bend 312, where it tapers at transition 314 to a smaller outer diameter entering the venotomy 316 and extending to its distal end 316. The larger diameter portion at bend 312 is more resistant to occlusion and kinking than if it were of the smaller diameter that is vascularly implanted. Catheter 302 may include a proximal end portion 320 with an even greater outer diameter adjacent to hub 308, if desired. For example, for a catheter having an outer diameter of 10 F within the vessel, the larger diameter of proximal portion 304 may be of 12 F, and the proximal end portion 320 may enlarge in a taper from 12 F to 13 F or 14 F.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of inserting a catheter into vasculature of a patient, comprising the steps of:
    providing a catheter having a first outer diameter extending proximally from a distal end thereof, and a proximal end having a second outer diameter larger than the first diameter, wherein the catheter has a tapered transition portion of limited length between said first outer diameter and said second outer diameter;
    providing a splittable introducer sheath and guide wire;
    inserting the introducer sheath into an incision in the vessel of a patient, and inserting the guide wire into a proximal sheath opening and through the introducer sheath and into the vessel at the vascular incision until a distal tip of the guidewire is at a desired location within the vessel;
    inserting the catheter over a proximal end of the guide wire and moving the catheter distally until a distal tip of the catheter has entered the vascular incision and the vessel along the guide wire;
    continuing to insert the catheter into the introducer sheath until the tapered transition portion of the catheter has entered the proximal sheath opening and has closed it off.

2. The method of claim 1, further including the step of splitting and removing the introducer sheath while continuing to urge the catheter into the vasculature of the patient.

3. The method of claim 2, further including the step of urging the tapered transition portion of the catheter into the vascular incision until the proximal end portion of the catheter has substantially closed off the vascular incision.

* * * * *